United States Patent
Holtermann et al.

(10) Patent No.: US 6,328,719 B1
(45) Date of Patent: Dec. 11, 2001

(54) FILTER AND GAS VENT SYSTEM INCORPORATED IN AN OSTOMY BAG

(75) Inventors: Henri Holtermann, Saint-Jean-de-Luz; Claude Hamelin, Ascain; Claude Dumartin, Saint-Jean-de-Luz, all of (FR)

(73) Assignee: B. Braun Medical Société Anonyme, Boulogne Billancourt (FR)

( * ) Notice: Subject to any disclaimer, the term of this patent is extended or adjusted under 35 U.S.C. 154(b) by 0 days.

(21) Appl. No.: 09/397,524

(22) Filed: Sep. 17, 1999

(30) Foreign Application Priority Data

Sep. 30, 1998 (FR) .................................................. 98 12214

(51) Int. Cl.⁷ ........................................................ A61F 5/44
(52) U.S. Cl. ............................................ 604/332; 604/333
(58) Field of Search .................................. 604/317, 327, 604/332, 333, 334, 337, 339

(56) References Cited

U.S. PATENT DOCUMENTS 4,367,742  1/1983  Ornstein .

FOREIGN PATENT DOCUMENTS

| 0 064 044 | 11/1982 | (EP) . |
| 0 068 964 | 1/1983 | (EP) . |
| 0 130 019 | 1/1985 | (EP) . |
| 2149306A * | 6/1985 | (GB) .................................. 604/332 |

* cited by examiner

Primary Examiner—Kim M. Lewis
(74) Attorney, Agent, or Firm—Oblon, Spivak. McClelland, Maier & Neustadt, P.C.

(57) ABSTRACT

A filter and gas vent system incorporated in an ostomy bag during its manufacture includes a filter in the shape of a flat band, its deodorizing core being left open to the ambient air at two ends of the filter. The latter is held inside the bag by two weld seams joining walls of the bag to each other. A key feature of the invention is that each of the two weld seams extends from one of two side edges of the bag to its upper edge. The filter can thus be contained entirely in the bag, which thus isolates the ends from the outside. The material from which the core of the filter is made, often activated charcoal, no longer risks soiling the clothes or being driven off when the subject is showering. This invention also prevents the liquid matter collected in the bag from seeping out by passing along the core of the filter.

6 Claims, 2 Drawing Sheets

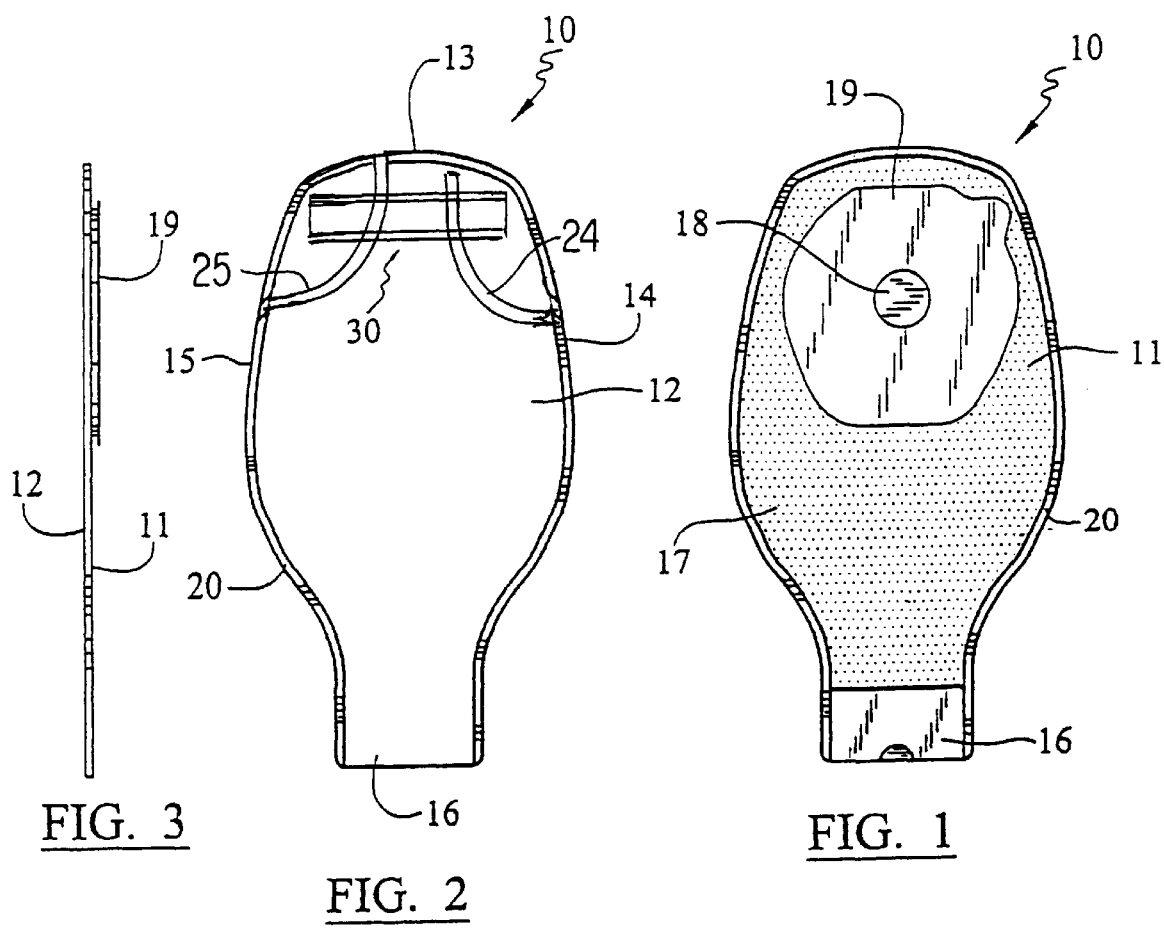
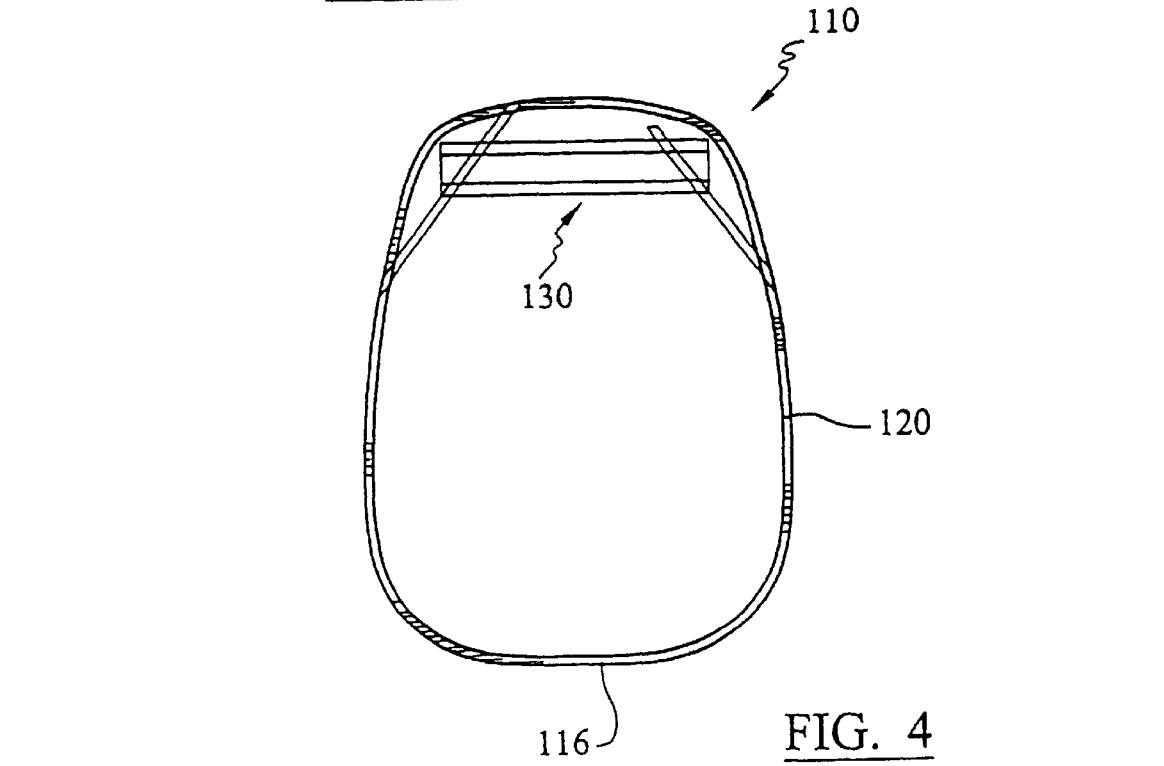

FILTER AND GAS VENT SYSTEM INCORPORATED IN AN OSTOMY BAG

BACKGROUND OF THE INVENTION

1. Field of the Invention

The present invention concerns a filter and gas vent system intended to be incorporated in an ostomy bag during its manufacture.

2. Discussion of the Background

Ostomy patients are patients who have undergone a surgical procedure such as a colostomy or ileostomy with creation of an artificial anus, which is also called by extension a "stoma". They are then provided with a collecting bag which is made up of two walls of impermeable plastic material which are welded to each other about the perimeter of the bag. One of these walls includes an opening for collecting the matter coming from the stoma. This opening is surrounded by a cutaneous protector intended to adhere in a practically leaktight manner to the abdominal wall of the ostomy patient for the purpose of holding the bag in place.

The matter collected in the bag is accompanied by intestinal gases whose evacuation is necessary in order to avoid excessive inflation of the bag. However, it is expedient to maintain a minimum residual pressure inside the bag. The reason is that, if this maintenance is not done, the two walls of the bag could stick to each other, and this sticking would impede the admission of matter into the bag. A slight cushioning effect also increases comfort by preventing the transmission of external pressures, especially those of clothes, to the stoma, which remains sensitive. For this purpose, the bag is provided with a gas vent. The latter is arranged above the opening in the bag through which the matter enters, such that the fecal matter, falling under gravity to the bottom of the bag, does not obstruct the vent.

Moreover, some intestinal gases release a foul odor which is embarrassing for the patient and for those around him or her. The vents are therefore provided with a deodorizing filter placed in the path of the gases in such a way that the intestinal gases pass through it and are purified before leaving the bag. In the earliest filter and vent systems, the filter was simply placed on the vent hole formed in one of the walls of the bag, depending on the circumstances either on the outside or on the inside of the bag. Then, in order to reduce the manufacturing costs and at the same time to avoid any moves having to be made by the ostomy patients, who are sometimes elderly or handicapped, attempts were made to incorporate the filters in the bag at the very moment of manufacture of the latter.

From the number of incorporated systems of this kind, mention may be made of European Patent No. 68,964 in the name of Laboratories Biotrol. This system is in the form of a disc of filtering material protected by a film. It is held in the peripheral weld seam of the bag so as to straddle the latter, thereby forming a filter with direct passage. Its exit face can open directly to the outside of the bag or alternatively to the inside of a downstream chamber which forms an integral part of the bag, or a complementary part, with walls that can be perforated to form a vent.

This system was then improved, especially as regards the length of travel of the gases and thus as regards its duration of effective operation, by the system forming the subject of French Patent No. 2 615 099. This system is in the form of a flat band and is made up of an elongate filtering core held between two protective films welded to each other on either side of the core. It is arranged between the two walls of the bag so as to extend horizontally from one side edge of the bag to the other. It is held in the peripheral weld seam of the bag in the area of each of these edges. The ends of the filter are free of film, so that the core communicates with the outside of the bag. The gases pass into the core via a hole formed in the protective film at the center of the filter. They thus travel half the width of the bag before being released to the outside via the ends of the filter.

The filter according to French Patent No. 2 615 099 which has just been described does have a disadvantage, however. This disadvantage is that the material composing its core rubs along the perimeter of the bag. Now, it contains activated charcoal which can come loose and soil the clothes. When the patient showers, the activated charcoal particles axe driven off in even greater quantities. The ends of the filter additionally clog up, preventing the filter from functioning. The fact that it is an integral part of the bag means that it is necessary to discard the whole bag. Moreover, the liquid matter inside the bag can pass along the activated charcoal and seep out and thus soil the clothes, at the same time causing unpleasant odors. It is conceivable to close off the ends of the filter with removable caps, but this arrangement is no more satisfactory than the filters attached afterwards to the bag, the ostomy patients often being elderly and infirm. Thus, it is a problem to develop an incorporated filter and vent system in which the core of the filter remains isolated from the outside of the bag.

SUMMARY OF THE INVENTION

With this aim in mind, the invention proposes a filter and gas vent system incorporated in an ostomy bag during its manufacture, said bag having an essentially horizontal upper edge and two essentially vertical side edges and being formed by two parallel walls which are welded to each other about a perimeter of the bag, one of them being provided with an opening for admission of matter into the bag, the filter in the shape of a flat band having two ends and being formed by a deodorizing core covered by at least one protective film impermeable to gases except at its two ends where the core is left open to the ambient air, the filter being held horizontally inside the bag, in its part situated above the opening for admission of matter, by two weld seams joining the two walls of the bag to each other and made in the area of the ends of the filter, characterized in that each of the two weld seams extends from one of the side edges of the bag to its upper edge, and in that the filter is contained entirely in the bag, which thus protects its ends.

Thus, compared to the filter and gas vent system known from French Patent No. 2 615 099, the filter is no longer held by the peripheral weld seam of the bag, but by the weld seams extending from the side edges of the bag to its upper edge. The filter can then stop before the peripheral weld seam, its ends opening out inside the compartments defined by the weld seams for holding the filter in place and by the peripheral weld seam.

According to one advantageous embodiment of the invention, one of the two weld seams holding the filter in place is incomplete, a narrow channel being left in immediate proximity to the upper edge for the passage of the gases. In this way, the matter cannot reach as far as the end of the filter located behind the incomplete weld seam and the corresponding side edge of the bag. The core of the filter is thus protected and does not risk becoming clogged up, preventing continued evacuation of the gases.

According to another advantageous embodiment of the invention, a vent hole is formed in one of the walls of the bag in the area of that end of the filter opposite the end held by the incomplete weld seam in such a way that the gases have to pass through the whole of the filter in order to reach the outside of the bag. This arrangement results in a longer travel of the gases than in the filter according to French Patent No. 2 615 099 cited above. Indeed, instead of passing through half the filter, the gases here travel its whole length. Consequently, with an identical deodorizing capacity, the filter does not have to be so long. This short length makes it possible to economize on material and thereby to reduce the overall manufacturing cost.

According to a further advantageous embodiment of the invention, a removable cap initially closes the vent so that it is possible to wait until a certain pressure of the gases is reached inside the bag before permitting evacuation of the gases.

It is also advantageous for the weld seams for holding the filter in place to be rectilinear.

Alternatively, the weld seams for holding the filter in place are curved inwardly.

Finally, it is advantageous for the core of the filter to be held between two protective films welded to each other on each side of the core.

Other advantages and characteristics of the present invention will become evident on reading the following non-limiting description of embodiments of incorporated filter and gas vent systems according to the invention, the description being made with reference to the attached drawings.

BRIEF DESCRIPTION OF THE DRAWINGS

FIG. 1 is a view, from the side facing the user's abdomen, of an open ostomy bag comprising as incorporated filter and gas vent system according to the invention;

FIG. 2 is a view of the bag in FIG. 1, from the side facing the clothes;

FIG. 3 is a side view of the bag in FIG. 1;

FIG. 4 is a view, from the side facing the clothes, of a closed ostomy bag comprising an incorporated filter and gas, vent system according to the invention;

DETAILED DESCRIPTION OF THE INVENTION

Figure 5:
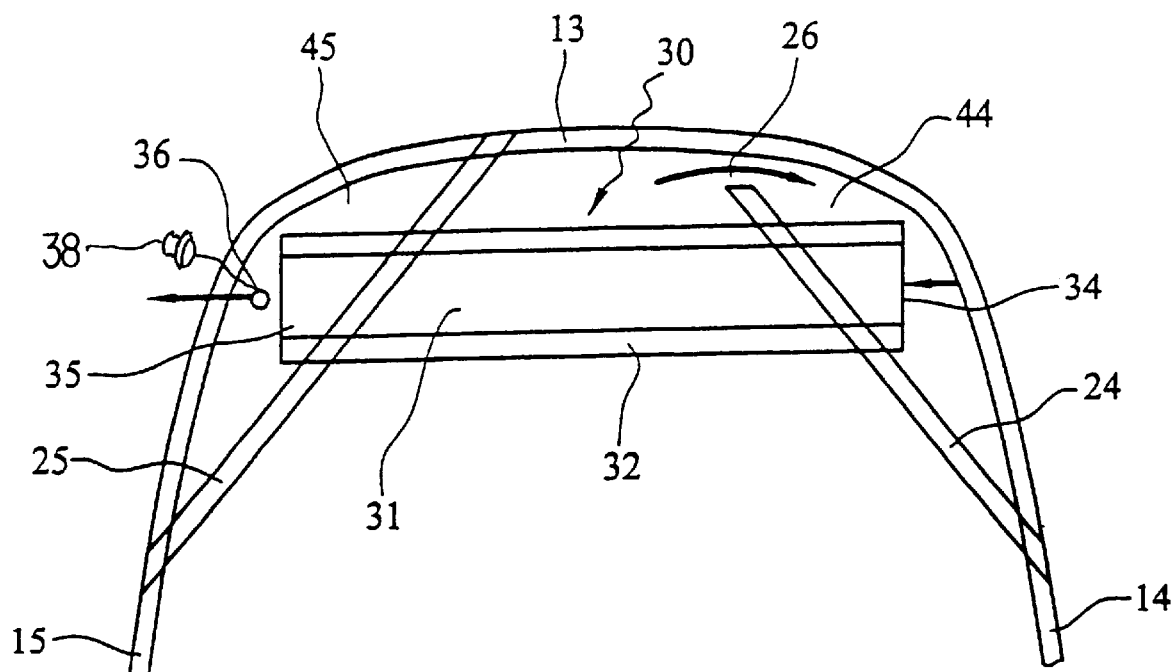
FIG. 5 is a detail view of a filter and gas vent system according to the invention.

FIG. 1 shows an ostomy bag 10 seen from the side intended to come into contact with the user's abdomen. As can also be seen from the side view in FIG. 3, the bag 10 is made up of two parallel walls 11 and 12 which are welded to each other about its perimeter 20 shown in FIG. 1. A lower edge 16 of the bag 10 is not closed, however, and the bag 10 is for this reason referred to as "open". This edge 16 continues via an extension whose sides are parallel in order to permit emptying of the bag. The extension is kept folded back on itself by a clip (not shown) in order to close the bag when the latter is in place for collecting matter. The walls 11 and 12 are made of a plastic material which is leaktight to liquids and gases. In order to prevent uncomfortable contact between this material and the skin of the user's abdomen, the corresponding wall 11 is covered with a lining 17 of woven fabric, felt or a nonwoven fabric.

Still on the abdomen side, the wall 11 has an opening 18 for admission of matter into the bag 10. A cutaneous protector 19 surrounds the opening 18. As can be seen from FIG. 3, the protector 19 protrudes from the wall 11 to which it is attached in particular by welding or bonding. The protector 19 can consist simply of a substrate covered with a pressure-sensitive adhesive or can additionally include an absorbent, consisting for example of hydrocolloids. The protector 19 allows the bag 10 to be held on the user's abdomen, with the stoma in line with the opening 18, in a relatively leaktight manner.

FIG. 2 shows the same bag 10, but seen this time from the side facing the user's clothes. The filter and gas vent system according to the invention can be seen here in the upper part of the bag 10. This upper part is represented in greater detail in FIG. 5. The invention can be adapted in the same way to a bag 110 referred to as "closed", such as that shown in FIG. 4, that is to say with a lower edge 116 being welded like the rest of a perimeter 120 of the bag 110.

Figure 6:
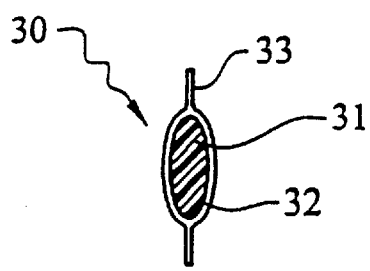
FIG. 6 is a section view of the filter in FIG. 5.

This system includes, in the first embodiment, a filter 30 in the shape of a flat band. This is designed like the filter which is the subject of French Patent No. No. 2 615 099 already discussed in the introductory part of this text. In summary, and as can be seen better from the section view in FIG. 6, the filter 30 is made up of a core 31 held between two protective films 32 which are welded to each other on either side of the core 31 in the area of margins 33. The core 31 has qualities of resistance to stresses as well as to chemical agents. The core 31 is most preferably an expanded plastic material with open cells. The latter are advantageously filled with activated charcoal combined, if appropriate, with ferric oxide in order to give the filter deodorizing qualities. As for the film 32, it is more preferably a plastic material which is gastight. At the ends of the filter 30, either the film 32 which covers the core 31 is porous, or the core 31 is left free exactly as in French Patent No. 2 615 099.

The filter 30 is also, held horizontally, as shown in FIG. 2, between the two walls 11 and 12 of the bag 10 by virtue of two weld seams 24 and 25 joining these walls to each other. Each of these weld seams 24 and 25 extends from a side edge 14 or 15 of the bag 10 to an essentially horizontal upper edge 13. In FIG. 5, the weld seams 24 and 25 are rectilinear, but there is nothing to prevent their being curved inwardly, for example with a concavity oriented towards the outside of the bag 10, as shown in FIG. 2. Thus, returning to FIG. 5, each of ends 34 and 35 of the filter 30 is situated in a compartment 44 or 45 defined by the weld seam 24 or 25 and by the corresponding side edge 14 or 15. In other words, the ends 34 and 35 remain inside the bag, thus isolating the activated charcoal from the user's clothes and from shower water.

Finally, a key feature of the system according to the present invention is that one of the weld seams, e.g. weld seam 24 situated on the right in FIG. 5, is not complete. A narrow channel 26 is left free between the weld seam 24 and that of the upper edge 13. The gases to be evacuated can pass through this channel 26 from the inside of the bag into the compartment 44 containing the end 34 of the filter 30. The travel of the gases is represented by arrows in FIG. 5. Once they have passed through the channel 26, they enter the filter via its end 34 and exit at the other end 35 of the filter 30. The latter end 35 is situated in the compartment 45 in the area of which the wall of the bag, facing the clothes, includes a vent hole 36. The vent hole 36, however, can only be pierced once a certain pressure level has been reached inside the bag. It can also be initially closed off by a removable cap 38 which the user takes off at the appropriate moment.

According to an alternative embodiment of the invention (not shown), a single protective film 32 is provided which is directly welded to the wall of the bag facing the clothes. However, it is still more economical to manufacture to the kilometer a filtering band having the cross section shown in FIG. 6 and to cut it to the length of the filters 30.

It will be clear that the invention is in no way limited to the embodiments described above with reference to the attached drawings and that it encompasses all modifications and variants deriving from the same basic principle.

What is claimed is:

1. Filter and gas vent system incorporated in an ostomy bag during its manufacture, comprising:

said bag having an essentially horizontal upper edge and two essentially vertical side edges and being formed by two parallel walls which are welded to each other about a perimeter of the bag, one of the walls being provided with an opening for admission of matter into the bag, said filter in the shape of a flat band having two ends and being formed by a deodorizing core covered by at least one protective film impermeable to gases except at the two ends where the core is left open to the ambient air, said filter being held horizontally inside the bag, in a part situated above the opening for admission of matter, by two weld seams joining the two walls of the bag to each other and made in the area of the two ends of the filter, each of the two weld seams extending from one of the side edges of the bag to the upper edge, said filter being contained entirely in the bag, which thus protects the two ends, one of the two weld seams holding the filter in place being incomplete, and a narrow channel being left in immediate proximity to the upper edge for the passage of the gases.

2. The filter and gas vent system according to claim 1, wherein a vent hole is formed in one of the walls of the bag in the area of the end of the filter opposite the end held by the incomplete weld seam in such a way that the gases have to pass through the whole filter in order to reach the outside of the bag.

3. The filter and gas vent system according to claim 2, wherein a removable cap initially closes the vent hole so that it is possible to wait until a certain pressure of the gases is reached inside the bag before permitting evacuation of the gases.

4. The filter and gas vent system according to claim 1, wherein the weld seams for holding the filter in place are rectilinear.

5. The filter and gas vent system according to claim 1, wherein the weld seams for holding the filter in place are curved inwardly.

6. The filter and gas vent system according to claim 1, wherein the core of the filter is held between two protective films welded to each other on each side of the core.

\* \* \* \* \*